United States Patent
Warthen et al.

(10) Patent No.: US 9,441,207 B2
(45) Date of Patent: Sep. 13, 2016

(54) METHOD OF REPLICATING VIRUSES IN SUSPENSION CULTURES OF DOG KIDNEY CELLS

(71) Applicant: Intervet Inc., Madison, NJ (US)

(72) Inventors: Monty R. Warthen, Fruitland, MD (US); William F. Skotta, Greenwood, DE (US)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/802,087

(22) Filed: Jul. 17, 2015

(65) Prior Publication Data

US 2015/0322411 A1 Nov. 12, 2015

Related U.S. Application Data

(63) Continuation of application No. 12/999,105, filed as application No. PCT/US2009/046721 on Jun. 9, 2009, now abandoned.

(60) Provisional application No. 61/061,828, filed on Jun. 16, 2008.

(51) Int. Cl.
*C12N 7/00* (2006.01)

(52) U.S. Cl.
CPC ........ *C12N 7/00* (2013.01); *C12N 2760/16151* (2013.01); *C12N 2760/16152* (2013.01); *C12N 2760/16251* (2013.01); *C12N 2760/16351* (2013.01)

(58) Field of Classification Search
None
See application file for complete search history.

(56) References Cited

U.S. PATENT DOCUMENTS

| | | | |
|---|---|---|---|
| 4,500,513 A | 2/1985 | Brown et al. | |
| RE33,164 E * | 2/1990 | Brown | A61K 39/145 424/209.1 |
| 6,656,720 B2 * | 12/2003 | Groner | A61K 39/145 435/235.1 |
| 6,825,036 B2 | 11/2004 | Makizumi et al. | |
| 7,160,699 B2 | 1/2007 | Wang et al. | |
| 2003/0044962 A1 | 3/2003 | Makizumi | |
| 2003/0203448 A1 | 10/2003 | Reiter et al. | |
| 2003/0229283 A1 | 12/2003 | Craig et al. | |
| 2004/0077086 A1 | 4/2004 | Reiter et al. | |
| 2004/0087020 A1 | 5/2004 | Olivieri et al. | |
| 2004/0171152 A1 | 9/2004 | Price et al. | |
| 2005/0089968 A1 | 4/2005 | Olivieri et al. | |
| 2006/0094104 A1 | 5/2006 | Grillberger et al. | |
| 2006/0286668 A1 | 12/2006 | Price et al. | |

FOREIGN PATENT DOCUMENTS

| | | |
|---|---|---|
| EP | 1 862 537 A1 | 12/2007 |
| EP | 1 260 581 B1 | 7/2010 |
| WO | 97/37000 A1 | 10/1997 |

OTHER PUBLICATIONS

ATCC catalog page for VR-317, A/Equine/2/Miami/63. copied in 2011.*
Klenk et al., "Activation of Influenza A Viruses by Trypsin Treatment", Virology, 1975, pp. 426-439, vol. 68.
Lazarowitz et al., "Enhancement of the infectivity of influenza A and B Viruses by Proteolytic Cleavage of the Hemagglutinin Polypeptide", Virology, 1975, pp. 440-454, vol. 68.
Tobita et al., "Plaque Assay and Primary Isolation of Influenza A Viruses in an Established Line of Canine Kidney Cells (MDCK) in the Presence of Trypsin", Medicinal Microbiology & Immunology, 1975, pp. 9-14, vol. 162.
Oxford et al., "Direct isolation in eggs of influenza A (H1N1) and B viruses with haemagglutinins of different antigenic and amino acid composition", Journal of General Virology, 1991, pp. 185-189, vol. 72.
Robertson et al., "The role of amniotic passage in the egg-adaptation of human influenza virus is revealed by haemagglutinin sequence analyses", Journal of General Virology, 1993, pp. 2047-2051, vol. 74.
International Search Report for corresponding PCT/US2009/046721, mailed Aug. 31, 2009.

* cited by examiner

*Primary Examiner* — Shanon A Foley
*Assistant Examiner* — Myron Hill

(57) ABSTRACT

Animal cells are described which can be infected by viruses and which are adapted to growth in suspension in medium free of animal-derived components, such as serum-free medium. Processes for the replication of viruses in cell culture using these cells are furthermore described, as well as vaccines which contain the viruses or antigenic portions thereof obtainable by the process.

20 Claims, No Drawings

METHOD OF REPLICATING VIRUSES IN SUSPENSION CULTURES OF DOG KIDNEY CELLS

RELATED APPLICATIONS

This application is a Continuation of copending U.S. application Ser. No. 12/999,105, filed on Dec. 15, 2010, which is a national stage entry under 35 U.S.C. §371 of PCT/US2009/046721 filed on Jun. 9, 2009, which claims priority to U.S. Provisional Application No. 61/061,828 filed on Jun. 16, 2008, the contents of which are hereby incorporated by reference in their entireties.

FIELD OF THE INVENTION

The present invention relates to animal cells which can be infected by viruses and are adapted to growth in suspension in medium free of animal-derived components, such as serum-free medium, and to processes for the replication of viruses in cell culture using these cells. The present invention further relates to the viruses obtainable by the process described and to vaccines which contain viruses of this type or constituents thereof.

BACKGROUND

Many vaccines including influenza vaccine for the treatment of humans and animals consist of one or more virus strains which have been replicated in embryonated hens' eggs. These viruses are isolated from the allantoic fluid of infected hens' eggs and their antigens are used in vaccines as intact virus particles, as virus particles disintegrated by detergents and/or solvents, as chemically or physically inactivated viruses, or as isolated, defined virus proteins as in subunit vaccines. The viruses are often inactivated by processes known to the person skilled in the art. The replication of live attenuated viruses, which are tested in experimental vaccines, is also carried out in embryonated hens' eggs.

The use of embryonated hens' eggs for vaccine production is time-, labor- and cost-intensive. The eggs, from healthy flocks of hens monitored by veterinarians, have to be incubated before infection, customarily for 12 days. Before infection, the eggs have to be selected with respect to living embryos, as only these eggs are suitable for virus replication. After infection the eggs are again incubated, customarily for 2 to 3 days. The embryos still alive at this time are killed by subjecting them to a cold environment, and the allantoic fluid is then obtained from the individual eggs by aspiration. By means of laborious purification processes, substances from the hen's egg that lead to undesired side effects of the vaccine are separated from the viruses, and the viruses are concentrated. As eggs are not sterile (pathogen-free), it is additionally necessary to remove and/or to inactivate pyrogens and all pathogens that are possibly present.

Viruses of other vaccines, such as, for example, rabies viruses, mumps, measles, rubella, polio viruses, tick bourne encephalits viruses such as Frühsommer-Meningo Ecephalitis (FSME) virus can be replicated in cell cultures. As cell cultures originating from tested cell banks are pathogen-free and, in contrast to hens' eggs, are defined virus replication systems that (theoretically) are available in almost unlimited amounts, they make possible economical virus replication under certain circumstances even in the case of influenza viruses. Moreover, the isolation and replication of influenza viruses in eggs leads to a selection of certain phenotypes, of which the majority differ from the clinical isolate. In contrast to this is the isolation and replication of the viruses in cell culture, in which no passage-dependent selection occurs (Oxford, J. S. et al., J. Gen. Virology 72(1991), 185-189; Robertson, J. S. et al., J. Gen. Virology 74 (1993) 2047-2051). For an effective vaccine, therefore, virus replication in cell culture is preferred.

It is known that influenza viruses can be replicated in cell cultures. Beside hens' embryo cells and hamster cells (BHK21-F and HKCC), MDBK and MDCK cells have been described as suitable cells for the in-vitro replication of influenza viruses (Kilbourne, E. D., in: Influenza, pages 89-110, Plenum Medical Book Company-New York and London, 1987). A prerequisite for a successful infection is the addition of proteases to the infection medium, preferably trypsin or similar serine proteases, as these proteases extracellularly cleave the precursor protein of hemagglutinin $[HA_0]$ into active hemagglutinin $[HA_1$ and $HA_2]$. Only cleaved hemagglutinin leads to the adsorption of the influenza viruses on cells with subsequent virus assimilation into the cells (Tobita, K. et al., Med. Microbiol. Immunol., 162 (1975), 9-14; Lazarowitz, S. G. & Choppin, P. W., Virology, 68 (1975) 440-454; Klenk, H.-D. et al., Virology 68 (1975) 426-439) and thus to a further replication cycle of the virus in the cell culture.

U.S. Pat. No. RE 33,164 (from U.S. Pat. No. 4,500,513), which is wholly incorporated by reference herein, described the replication of influenza viruses in cell cultures of adherently grown CLDK cells (or, "aCLDK cells"). The constraining requirement of growing these cells adherently places a limitation on the yield of cells that can be grown and also consequently places a limitation on the yield of virus that can be harvested for formulation in a vaccine.

Moreover, growing virus in adherent (or, substrate-dependent) cells requires steps not necessary when the cells can be grown in suspension. After cell proliferation, the nutrient medium is removed and fresh nutrient medium is added to the cells with infection of the cells with influenza viruses taking place simultaneously or shortly thereafter. A given time after the infection, protease (e.g. trypsin) is added in order to obtain an optimum virus replication. The viruses are harvested, purified and processed to give inactivated or attenuated vaccine.

Economical influenza virus replication as a prerequisite for vaccine production cannot be accomplished, however, using the methodology described in U.S. RE 33,164, as the change of media, the subsequent infection as well as the addition of trypsin, which is carried out later, necessitates opening the individual cell culture vessels several times and is thus very labor-intensive. Furthermore, the danger of contamination of the cell culture by undesirable microorganisms and viruses increases with each manipulation of the culture vessels. Yet another disadvantage with this system is that serum (including without limitation fetal calf serum, fetal bovine serum (fbs), newborn calf serum or bovine serum) is necessary for the growth of the cells. Serum contains trypsin inhibitors that interfere with viral yield.

A more cost-effective alternative is cell proliferation in systems where the cells do not need to be grown adherently to the culture container or on the surface of micro carriers. U.S. Pat. No. 6,656,720, which is wholly incorporated by reference herein, provides an example of one such method wherein MDCK cells that are grown in suspension are infected with influenza virus. However, additional cell lines and methodologies are needed that provide alternative means of growing viruses to increase efficiencies and reduce overall costs.

Hence, there is a need for additional cell lines that can be cultured in medium that is free of animal-derived components (e.g., serum-free medium or animal protein-free medium) to reduce the risk associated with use of animal by-products (e.g., bovine serum) and to eliminate the expense of such animal by-products. Furthermore, there is also a general need to eliminate the necessity of substrate-dependent growth (e.g., T-flask, roller bottle or micro carriers) and to have suspension cultures instead. Suspension cultures have numerous advantages over substrate-dependent growth including cost savings, higher cell densities and greater virus yields.

SUMMARY OF THE INVENTION

The present invention is directed to a method of replicating virus in a culture of sCLDK cells comprising: a) inoculating a suspension of sCLDK cells with a virus, thereby infecting the sCLDK cells; b) allowing the virus to reproduce in the infected sCLDK cells; and c) harvesting the virus from the suspension culture of sCLDK cells. The virus can be an influenza virus, such as a human influenza virus, an avian influenza virus, an equine influenza virus, a swine influenza virus, a canine influenza virus, or a feline influenza virus. Without limitation, the influenza virus can be an H1 influenza virus, an H2 influenza virus, an H3 influenza virus, an H5 influenza virus or an H7 influenza virus. Without limitation, the influenza virus can be an H5N1 influenza virus, an H3N8 influenza virus, an H1N1 influenza virus, an H3N2 influenza virus, an H2N3 influenza virus, an H7N8 influenza virus or an H3N1 influenza virus. In an embodiment of the invention, shortly before inoculating, simultaneously with inoculating, or shortly after inoculating, a protease to cleave the precursor protein of hemagglutinin is added to the suspension of sCLDK cells. The protease can be trypsin.

The present invention is also directed to a process of adapting substrate-dependent CLDK cells for growth in suspension comprising a) inoculating a sample of substrate-dependent CLDK cells in a medium comprising serum substitutes; b) growing the cells in suspension in the medium; c) serially passaging the CLDK cells in suspension in fresh batches of the medium; and d) weaning the CLDK cells in suspension off of the serum substitutes by reducing the amount of the serum substitutes in the medium to zero. This process is also referred to as “the adaptation process.” The medium can be serum-free. The medium can also be free of any animal derived components.

In one embodiment of the adaptation process, the cells are serially passaged in step (c) until the seven day growth factor is at least from about 3 to 20, preferably greater than about 5, more preferably greater than about 7, most preferably greater than about 10. After the average growth factor for 3 to 15 serial passages of step (c) has achieved such values, the CLDK cells in suspension can be weaned off of the serum substitutes over the subsequent 3 to 6 passages. As a non-limiting example, CLDK cells are serially passaged in suspension until the average growth factor of at least 5-10 passages in suspension is greater than about 5, at which point they are weaned off of the serum substitute over the subsequent 6 or fewer passages. Preferably, the CLDK cells are serially passaged in suspension until the average growth factor of at least 10 passages in suspension is greater than about 8, at which point they are weaned off of the serum substitute over the subsequent 6 or fewer passages. Alternatively, the CLDK cells are serially passaged in suspension until the average growth factor of at least 5 passages in suspension is greater than about 12, at which point they are weaned off of the serum substitute over the subsequent 6 or fewer passages.

The CLDK cells can successfully be weaned off of the serum substitutes in the adaptation process providing that the 7 day growth factor of the passage immediately prior to the first weaning passage is at least 5. Preferably, the 7 day growth factor of the last passage immediately prior to the weaning passage is at least 7, more preferably at least 10, even more preferably at least about 13.

The present invention is also directed to a method of continuously propagating sCLDK cells in suspension comprising: a) inoculating sCLDK cells into a medium; b) growing the sCLDK cells in suspension for a period of from about 4 to 10 days; c) transferring a sample of cultured material from (b) into fresh cell-free medium; d) and repeating (b) and (c) for a period of continuous growth. The medium can be serum-free. The medium can be animal protein-free. The sample can be transferred to the fresh cell-free medium without the prior addition of any protease. The cell density after transferring the sample according to (c) can be at least $3\times10^5$ cells/mL, and is preferably at least $5\times10^5$ cells/mL. The sCLDK cells can have a growth factor greater than 3 over a 4-10 day period, preferably a growth factor greater than about 5, most preferably greater than about 10, over a 4-10 day period.

The present invention is also directed to sCLDK cells capable of growing in suspension obtainable by the adaptation process. As described above, the adaptation process is the process of adapting substrate-dependent CLDK cells for growth in suspension comprising a) inoculating a sample of substrate-dependent CLDK cells in a medium comprising serum substitutes; b) growing the cells in suspension in the medium; c) serially passaging the CLDK cells in suspension in fresh batches of the medium; and d) weaning the CLDK cells in suspension off of the serum substitutes by reducing the amount of the serum substitutes in the medium to zero. The medium can be serum-free. The serum substitutes can be animal-protein free. The present invention is also directed to use of such sCLDK cells obtained by this process for replicating virus. The present invention is also directed to use of such virus replicated in such sCLDK cells obtained by this process in the manufacture of a vaccine.

The present invention is also directed to a composition comprising cell culture medium and sCLDK cells.

The present invention also relates to a method of making a vaccine comprising a) inoculating medium with sCLDK cells; b) growing the sCLDK cells in suspension in the medium, thereby generating a suspension of sCLDK cells; c) incubating the suspension of sCLDK cells with virus thereby generating a suspension of infected sCLDK cells; d) allowing the virus to reproduce in the infected sCLDK cells; e) harvesting or isolating the virus; and f) mixing the harvested or isolated virus with one or more pharmaceutically acceptable carrier thereby making a vaccine.

DETAILED DESCRIPTION

The present invention relates to making available cells and processes that make possible simple and economical virus replication in cell culture. The invention thus relates to animal cells that can be infected by viruses and that are adapted to growth in suspension in serum-free or animal protein-free medium. It was found that it is possible with the aid of cells of this type to replicate viruses in cell culture in a simple and economical manner. Because the cells are adapted for growth in suspension, production batches yield greater numbers of cells and subsequently higher titers of virus. A greater yield of virus reduces overall costs of production. A further advantage is that the consumption of media is markedly decreased, thereby reducing total media costs. Also importantly, an advantage of the present invention is growth of cells (and subsequent replication of viruses) in medium that is free of any animal derived components, such as bovine serum or fetal calf serum, thereby eliminating the risk of various pathogens including without limitation TSE (transmissible spongiform encephalopathy).

Moreover, by the use of the cells according to the invention, on the one hand a change of medium before infection to remove serum can be dispensed with and on the other hand the addition of protease (where needed) can be carried out simultaneously with the infection. On the whole, only a single opening of the culture vessel for infection with viruses is necessary, whereby the danger of the contamination of the cell cultures is drastically reduced. The expenditure of effort that would be associated with the change of medium, the infection and the subsequent protease addition is furthermore decreased.

The cells used according to the invention are derived from substrate-dependent Cutter Laboratory Dog Kidney (CLDK) cells. As used herein, "substrate-dependent CLDK cells" and like terms are used interchangeably with "adherent CLDK cells," "aCLDK cells" or like terms. aCLDK cells are different from suspension CLDK cells. Whereas the former grow adherently, the latter grow in suspension, such as in a shaker flask or other large-scale production container including without limitation disposable or non-disposable bioreactors or biocontainers. aCLDK cells require a surface on which to grow, such as the surface of a roller bottle or microcarriers or beads added to the medium. aCLDK cells do not grow in suspension. When inoculated into medium in a shaker flask placed on an oscillating platform, aCLDK cells may maintain some viability, but do not grow. Rather, aCLDK cells tend to clump together.

Suspension CLDK cells are also termed "sCLDK" cells or "sCLDK-SF" cells to indicate that they grow in a serum-free media. sCLDK cells are derived from aCLDK cells by passaging through serum-free medium in suspension as described herein. On account of these properties and their ability to serve as host cells for replicating viruses, sCLDK cells are suitable for economical replication of viruses in cell culture by means of a simple and cost-effective process. In contrast to aCLDK cells, sCLDK cells do grow in a shaker flask placed on an oscillating platform or in other suspension growth means. Not only do sCLDK cells maintain viability in such suspended growth conditions, but they can multiply in number without aggregating or clumping as is the case with aCLDK cells.

As described further below, sCLDK cells have several advantages over aCLDK cells. First, unlike aCLDK cells, sCLDK cells grow in suspension. Unlike aCLDK cells, sCLDK cells have a growth factor of at least three (3) when passed into fresh media for growth in suspension over a 4-10 day period. In an embodiment of the invention, the sCLDK cells described herein grow in suspension by a factor of greater than 3, preferably greater than 5, in a 4-10 day period. More preferably, the sCLDK cells described herein grow in suspension by a factor of greater than about 6, most preferably greater than about 10, in a 4-10 day period.

Unlike aCLDK cells, sCLDK cells are also able to grow continuously in suspension. sCLDK cells can grow continuously in suspension by a factor of greater than 3, preferably greater than 5, when passed into fresh media every 4-10 days. More preferably, the sCLDK cells described herein can grow continuously in suspension by a factor of greater than about 6, most preferably greater than about 10, when passed into fresh media every 4-10 day period.

Another advantage of sCLDK cells over aCLDK cells is that the former can grow in the absence of serum or other animal derived media supplements. Unlike aCLDK cells, sCLDK cells on average at least triple when passed into fresh media containing no serum or other animal derived media supplements over a 4-10 day period. In an embodiment of the invention, the sCLDK cells described herein grow in media containing no serum or other animal derived media supplements by a factor of greater than 3, preferably greater than 5, in a 4-10 day period. More preferably, the sCLDK cells described herein grow when passed into fresh media containing no serum or other animal derived media supplements by a factor of greater than about 6, most preferably greater than about 10, in a 4-10 day period.

Unlike aCLDK cells, sCLDK cells are also able to grow continuously in media containing no serum or other animal derived components. sCLDK cells can grow continuously in media containing no serum or other animal derived components by a factor of greater than 3, preferably greater than 5 when passed into fresh media every 4-10 days. More preferably, the sCLDK cells described herein can grow continuously in media containing no serum or other animal derived components by a factor of greater than about 6, most preferably greater than about 10, when passed into fresh media every 4-10 days.

Hence, an advantage of sCLDK cells is their ability to grow continuously in suspension in media containing no serum or other animal derived components. sCLDK cells can grow continuously in suspension in media containing no serum or other animal derived components by a factor of greater than 3, preferably greater than 5, when passed into fresh media every 4-10 days. More preferably, the sCLDK cells described herein can grow continuously in suspension in media containing no serum or other animal derived components by a factor of greater than about 6, most preferably greater than about 10, when passed into fresh media every 4-10 day period.

As used herein, "growth factor" or like terms refer to the multiplicative value by which an initial cell population has grown over a period of time. Hence, a growth factor of 2 or 3 indicates that the cell density has respectively doubled or tripled relative to the starting cell density when cells were passed (i.e., inoculated or planted) into the fresh media. A growth factor of 10 or 20 indicates that the cell density has respectively multiplied by a factor of 10 or 20 relative to the starting cell density when the cells were passed into the fresh media. A growth factor of 1 or less indicates that the cell density did not increase or that the cell population has declined.

The present invention therefore also relates to a process for the replication of viruses in cell culture in which cells according to the invention are used. In particular the process that comprises the following steps: i) proliferation of the cells according to the invention described above in serum-free medium in suspension; ii) infection of the cells with viruses; iii) culturing of the infected cells; and iv) isolation of the replicated viruses. Where titer can be increased as in the case of influenza virus, protease can be added shortly before, simultaneously to or shortly after infection. In one non-limiting embodiment of the invention, sCLDK cells are grown in a serum free media to replicate influenza virus. The skilled artisan is aware of other viruses that can be replicated in the sCLDK cells described herein, and is not limited to replication of influenza viruses.

The present invention is also directed to a method of replicating virus in a culture of sCLDK cells comprising: a) inoculating a suspension of sCLDK cells with a virus, thereby infecting the sCLDK cells; b) allowing the virus to reproduce in the infected sCLDK cells; and c) harvesting the virus from the suspension culture of sCLDK cells. The virus can be harvested through centrifugation, filtration or other mechanical or biochemical separation means of the infected cell suspension. Hence, harvested virus can include virus in the presence of sCLDK cells or sCLDK cell debris. Harvested virus can also include virus in the absence of sCLDK cells or sCLDK cell debris.

The cells according to the invention can preferably be cultured in media free of animal derived components (e.g., serum-free media, animal protein-free media) known to the person skilled in the art. Non-limiting examples of such media include Iscove's medium, ultra CHO medium (BioWhittaker), EX-CELL™ MDCK serum-free medium (JRH Biosciences, Lenexa, Kans.)). Other serum-free media that may be used according to the present invention include EX-CELL™ 520 medium (JRH Biosciences, Lenexa, Kans.) and HyQ PF CHO medium (Hyclone, Logan, Utah). Other animal protein-free media that may be used according to the present invention include EX-CELL™ 302 medium (JRH Biosciences, Lenexa, Kans.), HyQ PF CHO MPS medium (Hyclone, Logan, Utah) and Rencyte BHK medium (Medicult, Jyllinge, Denmark). Other soy- or yeast-based animal protein-free media that may be used according to the invention include those described in U.S. Pat. No. 7,160,699 or U.S. Published Patent Applications No. 2003/0203448, 2004/0077086, 2004/0087020, 2004/0171152, 2005/0089968, 2006/0094104, 2006/0286668, which are all hereby incorporated by reference in their entirety. Suitable culture vessels that can be employed in the course of the process according to the invention are all vessels known to the person skilled in the art.

Serum substitutes can be added to the animal-derived component-free media. Such substitutes are themselves free of any animal-derived components, yet may contain recombinant animal proteins expressed in cells that were preferably cultured in media free of animal-derived components. Serum substitutes can contain recombinant growth factors, transferrin substitutes or recombinant transferrin substitutes, synthetic hormones and/or other recombinant proteins. Serum substitutes are free of any adventitious viruses because the recombinant protein components are manufactured in a controlled environment in pathogen-free or viral-free cells. Hence, serum substitutes have no virus or TSE (transmissible spongiform encephalopathy) risk. Serum substitutes are preferably used to adapt adherent CLDK cells for growth in suspension (i.e., transform aCLDK cells to sCLDK cells). However, such substitutes can also be used for culturing sCLDK cells in suspension for growth of virus according to the present invention. A non-limiting example of a serum substitute includes LIPUMIN™ serum substitute (PAA Laboratories GmbH, Pasching, Austria).

The temperature for the proliferation of the cells before infection as in the case with influenza viruses is preferably 37° C. Culturing for proliferation of the cells can be carried out in a perfusion system, e.g. in a stirred vessel fermenter, using cell retention systems known to the person skilled in the art, such as, for example, centrifugation, filtration, spin filters and the like, using batch processes or using other techniques well known to the skilled artisan.

The cells are in this case preferably proliferated for 2 to 18 days, particularly preferably for 3 to 11 days. Exchange of the medium is carried out in the course of this, increasing from 0 to approximately 1 to 3 volumes per day. The cells are proliferated up to very high cell densities in this manner, preferably up to approximately $2 \times 10^7$ cells/ml. Perfusion rates during culture in a perfusion system can be regulated both via the cell count, the content of glucose, glutamine or lactate in the medium and via other parameters known to the person skilled in the art. In the case of infection with influenza viruses, about 85% to 99%, preferably 93 to 97%, of the fermenter volume is transferred with cells to a further fermenter. The cells remaining in the first fermenter can in turn be mixed with medium and replicated further in the perfusion system. In this manner, continuous cell culture for virus replication is available.

In a preferred embodiment of the process according to the invention, the pH of the culture medium used can be regulated during culturing and is in the range from pH 6.6 to pH 7.8, preferably in the range from pH 6.8 to pH 7.3.

Furthermore, the $pO_2$ value is advantageously regulated in this step of the process and is preferably between 25% and 95%, in particular between 35% and 60% (based on the air saturation). According to the invention, the infection of the cells cultured in suspension is preferably carried out when the cells in the batch process have achieved a cell density of about 8 to $25 \times 10^5$ cells/ml or about 5 to $20 \times 10^6$ cells/ml in the perfusion system.

In a further preferred embodiment, the infection of the cells in the case of influenza viruses is carried out at an m.o.i. (multiplicity of infection) of about 0.0001 to 10, preferably of 0.002 to 0.5. The addition of the protease, which brings about the cleavage of the precursor protein of hemagglutinin [$HA_0$] and thus the adsorption of the viruses on the cells, can be carried out according to the invention shortly before, simultaneously to or shortly after the infection of the cells with influenza viruses. If the addition is carried out simultaneously with the infection, the protease can either be added directly to the cell culture to be infected or, for example, as a concentrate together with the virus inoculate. The protease is preferably a serine protease, and particularly preferably trypsin.

In a preferred embodiment, trypsin is added to the cell culture to be infected to a final concentration of 1 to 200 µg/ml, preferably 5 to 50 µg/ml, and particularly preferably 5 to 30 µg/ml in the culture medium. During the further culturing of the infected cells according to the invention, trypsin reactivation can be carried out by fresh addition of trypsin in the case of the batch process or in the case of the perfusion system by continuous addition of a trypsin solution or by intermittent addition. In the latter case, the trypsin concentration is preferably in the range from 1 µg/ml to 80 µg/ml.

After infection, the infected cell culture is cultured further to replicate the viruses, in particular until a maximum cytopathic effect or a maximum amount of virus antigen can be detected. Preferably, the culturing of the cells is carried out for 2 to 10 days, in particular for 3 to 7 days. The culturing can in turn preferably be carried out in the perfusion system or in the batch process.

In a further preferred embodiment, the cells can be cultured at a temperature of 30° C. to 37° C. in an incubator set at 5-15% $CO_2$, most preferably around 10% $CO_2$.

The culturing of the cells after infection as in the case of influenza viruses is in turn preferably carried out at regulated pH and $pO_2$. The pH in this case is preferably in the range of from 6.6 to 7.8, particularly preferably from 6.8 to 7.2, and the $pO_2$ in the range of from 25% to 150%, preferably from 30% to 75%, and particularly preferably in the range of from 35% to 60% (based on the air saturation).

During the culturing of the cells or virus replication of the process, a substitution of the cell culture medium with freshly prepared medium, medium concentrate or with defined constituents such as amino acids, vitamins, lipid fractions, phosphates etc. for optimizing the antigen yield is also possible.

After infection as in the case with influenza viruses, the cells can either be slowly diluted by further addition of medium or medium concentrate over several days or can be incubated during further perfusion with medium or medium concentrate decreasing from approximately 1 to 3 to 0 fermenter volumes/day. The perfusion rates can in this case in turn be regulated by means of the cell count, the content of glucose, glutamine, lactate or lactate dehydrogenase in the medium or other parameters known to the person skilled in the art.

A combination of the perfusion system with a fed-batch process is further possible. In a preferred embodiment of the process, the harvesting and isolation of the replicated virus (e.g., influenza virus) is carried out within 2 to 10 days, preferably 3 to 7 days, after infection. To do this harvesting, for example, the cells or cell residues are separated from the culture medium by means of methods known to the person skilled in the art, for example by centrifugation, separators or filters. Following such steps, the concentration of the virus present in the culture medium is carried out by methods known to the person skilled in the art, such as, for example, gradient centrifugation, filtration, precipitation and the like.

The invention further relates to influenza viruses that are obtainable by a process according to the invention. They can be harvested and formulated by known methods to give a vaccine for administration to humans or animals. The immunogenicity or efficacy of a vaccine comprising the influenza viruses obtained can be determined by methods known to the person skilled in the art, e.g., by means of the protection imparted in the loading experiment or as antibody titers of neutralizing antibodies. The determination of the amount of virus or antigen produced can be carried out, for example, by the determination of the amount of hemagglutinin according to methods known to the person skilled in the art. It is known, for example, that cleaved hemagglutinin binds to erythrocytes of various species, e.g. to chicken erythrocytes. This makes possible a simple and rapid quantification of the viruses produced or of the antigen formed.

Thus the invention also relates to vaccines that contain virus obtainable from the process according to the invention. Vaccines of this type can optionally contain the additives customary for vaccines, in particular substances that increase the immune response, i.e., adjuvants, e.g. hydroxide of various metals, carbomers, constituents of bacterial cell walls, oils or saponins, and customary pharmaceutically tolerable excipients.

The viruses can be present in the vaccines as intact virus particles, in particular as live attenuated viruses. For this purpose, virus concentrates are adjusted to the desired titer and either lyophilized or stabilized in liquid form.

In a further embodiment, the vaccines according to the invention can contain disintegrated, inactivated or intact but inactivated viruses. For this purpose, the infectiousness of the virus is destroyed by means of chemical and/or physical methods (e.g., by detergents or formaldehyde). The vaccine is then adjusted to the desired amount of antigen and after possible admixture with adjuvants or after possible vaccine formulation, dispensed, for example, in liposomes, microspheres or other "slow release" formulations.

In a further preferred embodiment, the vaccines according to the invention can finally be present as subunit vaccine, i.e. they can contain defined, isolated virus constituents, preferably isolated proteins of the influenza or other virus. These constituents can be isolated from the virus by methods known to the person skilled in the art.

Furthermore, influenza or other viruses obtained by the process according to the invention can be used for diagnostic purposes. Thus the present invention also relates to diagnostic compositions that contain influenza or other viruses according to the invention or constituents of such viruses, if appropriate, in combination with additives customary in this field and suitable detection agents.

The following examples are merely illustrative, and not limiting to the remainder of this disclosure in any way.

EXAMPLES

Example 1A

Adaptation of CLDK Cells for Serum-Free or Serum Substitute-Free Suspended Growth Cutter Laboratory Dog Kidney (CLDK) cells are anchorage dependent, and hence require a substrate or surface on which to grow. Suitable substrates include the interior surfaces of containers such as T-flasks or roller bottles, or upon the surface of beads or microcarriers that can be added to a culturing container. Typically, these cells form monolayers on the substrate, and can be grown in static culture and roller bottle. These cells require serum to grow and are epithelial in morphology.

Two ampoules of Cutter Laboratories aCLDK cells were thawed, and then transferred to two 4 mL cryotubes such that there was 1 mL of thawed material in each tube. 1 mL of supplemented EX-CELL™ MDCK serum-free medium was added to each cryotube. "Supplemented EX-CELL™ MDCK serum-free medium" as used herein refers to a mixture of EX-CELL™ MDCK serum-free medium (SAFC Biosciences, Lenexa, Kans.) supplemented with L-glutamine (20 mLs of 200 mM solution/L of medium) and gentamicin (0.5 mL of 100 g/mL solution for every liter of medium). After allowing the two cryotubes to sit undisturbed for 3-5 minutes, all of the material was transferred to two 15 mL centrifuge tubes. Approximately 8 mLs of supplemented EX-CELL™ MDCK serum-free medium was added to each 15 ml centrifuge tube. These two tubes were then allowed to sit undisturbed for 3-5 minutes, after which time the two tubes were centrifuged for ten minutes at about 1,000 rpms (500×g). The media supernatant was discarded and the pelleted cells were resuspended in a total of 20 mLs of supplemented EX-CELL™ MDCK serum-free medium. The resuspended cells were transferred to a 125 mL shaker flask fitted with a 0.2µ vented cap (Corning Inc., Corning, N.Y.), to which 30 mLs of additional supplemented EX-CELL™ MDCK serum-free medium was added to bring the total volume to 50 mLs. These cells correspond to passage no. 1 in Table 1 below and were placed on an orbital shaker plate in a 37° C. water jacketed incubator with a 10% $CO_2$ feed for a week.

Cells were passed on a weekly basis two more times (passages 2 and 3 in Table 1) without serum or serum substitutes and in shaker flasks so as to require any growth to be in suspension. However, as shown in Table 1, the highest recorded growth factor for the aCLDK cells under these conditions was less than 3 per 7-day period. The subsequent 13 passages also included 1% Pluronic® F68 surfactant (Invitrogen Corp., Carlsbad, Calif.) in the culturing media. During this time, cells remained highly viable but continued to have a growth factor that was (on average) less than 2 per 7-day period, as shown in Table 1. The next 14 passages also included 1% Lipumin™ ADCF (animal derived component free) serum substitute (PAA Laboratories GmbH, Pasching, Austria) in the media. During these passages, the average growth factor (as shown in Table 1) was greater than 12 and the cells were >95% viable. In the following passage, cells were weaned to 0.5% Pluronic® F68 surfactant and 0.5% Lipumin™ ADCF serum substitute. In the next passage, cells were weaned to 0.25% Pluronic® F68 surfactant and 0.25% Lipumin™ ADCF serum substitute. The subsequent 6 passages had the cells completely free of Pluronic® F68 surfactant and Lipumin™ ADCF serum substitute. During these last 6 passages, the cells had a growth factor on average greater than 17 (as shown in Table 1) and continued to have high viability.

Table 1 shows the passage history described in this example. Supplemented EX-CELL™ MDCK serum-free medium was used in every passage with the indicated amount of Pluronic® F68 surfactant or Lipumin™ ADCF serum substitute as shown, for a total volume of 50 mLs. Each passage was into a 125 mL shaker flask and placed on an orbital shaker plate in a 37° C. water jacketed incubator with a 10% $CO_2$ feed for a week. The "Cell Plant Density" refers to the concentration of cells in the 50 mLs of medium at the beginning of the passage (i.e., the beginning of the week) and is given in cells/mL. After a week, the cells were counted from a sample of material to determine the "Cell count/mL." The "7-Day Growth Factor" was determined by dividing the "Cell count/mL" value by the "Cell Plant Density" value.

TABLE 1

Passage History to Adapt aCLDK Cells to sCLDK-SF Cells

| Passage | % Pluronic® F68 Surfactant | % Lipumin™ ADCF Serum Substitute | Cell Plant Density (cells/mL) | Cell count/mL | 7-Day Growth Factor |
|---|---|---|---|---|---|
| 1 | 0 | 0 | NA* | NA | NA |
| 2 | 0 | 0 | NA | $2.10 \times 10^5$ | NA |
| 3 | 0 | 0 | $2.00 \times 10^5$ | $4.89 \times 10^5$ | 2.45 |
| 4 | 1 | 0 | $2.00 \times 10^5$ | $2.24 \times 10^5$ | 1.12 |
| 5 | 1 | 0 | $2.00 \times 10^5$ | $2.15 \times 10^5$ | 1.08 |
| 6 | 1 | 0 | $5.00 \times 10^5$ | $6.39 \times 10^5$ | 1.28 |
| 7 | 1 | 0 | $5.00 \times 10^5$ | $6.54 \times 10^5$ | 1.31 |
| 8 | 1 | 0 | $5.00 \times 10^5$ | $5.13 \times 10^5$ | 1.03 |
| 9 | 1 | 0 | $5.00 \times 10^5$ | $6.92 \times 10^5$ | 1.38 |
| 10 | 1 | 0 | $5.00 \times 10^5$ | $6.96 \times 10^5$ | 1.39 |
| 11 | 1 | 0 | $5.00 \times 10^5$ | $7.19 \times 10^5$ | 1.44 |
| 12 | 1 | 0 | $5.00 \times 10^5$ | $5.57 \times 10^5$ | 1.11 |
| 13 | 1 | 0 | $5.00 \times 10^5$ | $7.24 \times 10^5$ | 1.45 |
| 14 | 1 | 0 | $5.00 \times 10^5$ | $5.51 \times 10^5$ | 1.10 |
| 15 | 1 | 0 | $5.00 \times 10^5$ | $4.74 \times 10^5$ | 0.95 |
| 16 | 1 | 0 | $4.00 \times 10^5$ | $6.92 \times 10^5$ | 1.73 |
| 17 | 1 | 1 | $5.00 \times 10^5$ | $3.61 \times 10^5$ | 0.72 |
| 18 | 1 | 1 | $3.00 \times 10^5$ | $1.62 \times 10^6$ | 5.40 |
| 19 | 1 | 1 | $5.00 \times 10^5$ | $2.10 \times 10^6$ | 4.20 |
| 20 | 1 | 1 | $5.00 \times 10^5$ | $5.63 \times 10^6$ | 11.26 |
| 21 | 1 | 1 | $5.00 \times 10^5$ | $8.79 \times 10^6$ | 17.58 |
| 22 | 1 | 1 | $5.00 \times 10^5$ | $5.21 \times 10^6$ | 10.42 |
| 23 | 1 | 1 | $5.00 \times 10^5$ | $3.25 \times 10^6$ | 6.50 |
| 24 | 1 | 1 | $5.00 \times 10^5$ | $3.63 \times 10^6$ | 7.26 |
| 25 | 1 | 1 | $5.00 \times 10^5$ | $7.21 \times 10^6$ | 14.42 |
| 26 | 1 | 1 | $5.00 \times 10^5$ | $1.17 \times 10^7$ | 23.40 |
| 27 | 1 | 1 | $5.00 \times 10^5$ | $8.68 \times 10^6$ | 17.36 |
| 28 | 1 | 1 | $5.00 \times 10^5$ | $1.02 \times 10^7$ | 20.37 |
| 29 | 1 | 1 | $5.00 \times 10^5$ | $8.50 \times 10^6$ | 17.00 |
| 30 | 1 | 1 | $5.00 \times 10^5$ | $8.08 \times 10^6$ | 16.16 |
| 31 | 0.5 | 0.5 | $5.00 \times 10^5$ | $6.80 \times 10^6$ | 13.60 |
| 32 | 0.25 | 0.25 | $5.00 \times 10^5$ | $3.19 \times 10^7$ | 63.80 |
| 33 | 0 | 0 | $5.00 \times 10^5$ | $5.30 \times 10^5$ | 1.06 |
| 34 | 0 | 0 | $5.00 \times 10^5$ | $9.96 \times 10^6$ | 19.92 |
| 35 | 0 | 0 | $5.00 \times 10^5$ | $9.10 \times 10^6$ | 18.20 |
| 36 | 0 | 0 | $5.00 \times 10^5$ | $1.03 \times 10^7$ | 20.50 |
| 37 | 0 | 0 | $5.00 \times 10^5$ | $3.42 \times 10^6$ | 6.84 |
| 38 | 0 | 0 | $5.00 \times 10^5$ | $1.99 \times 10^7$ | 39.80 |

*NA: not available

From the cells of the 38th passage, a small cell stock (15-20 cryovials) was frozen in ampoules and stored in liquid nitrogen (LN) with 10% DMSO (Sigma-Aldrich Co., St. Louis, Mo.). The designation was changed to sCLDK-SF, referring to "s" as suspension and "-SF" as serum free during this process. No serum was utilized in the freezing of this cell line.

Approximately five months after freezing vials after the 38th passage, two of the frozen vials were thawed and placed in a shaker flask. These cells were grown for one week in a 125 mL shaker flask (passage no. 39). These cells were then scaled up (over two more passages) to 4400 mL using eleven 1 L Nalgene shaker flasks, each fitted with a 0.2μ, vented cap. Day four (96 hours) into passage no. 41, log-phase (actively growing) cells were harvested, 10% DMSO was added and glass ampoules were filled and sealed with an automated ampoule filling and sealing machine under HEPA filtered air. The master cell stock bank was inspected for proper seals, labeled and frozen in liquid nitrogen. Several frozen samples were thawed and screened for potential contaminates (mold and bacterial contamination). Screening revealed no bacterial or mold growth after 21 days in tryptone soy broth and tryptose phosphate broth at 28° C. and 37° C., respectively.

Example 1B

Adaptation of aCLDK Cells for Serum-Free or Serum Substitute-Free Suspended Growth The above CLDK adaptation procedure was subsequently repeated and completed with fewer passages. The following table summarizes the culture media and observed growth for this subsequent procedure.

TABLE 2

Passage History to Adapt aCLDK Cells to sCLDK-SF Cells

| Passage | % Pluronic® F68 Surfactant | % Lipumin™ ADCF Serum Substitute | Cell Plant Density (cells/mL) | Cell count/mL | 7-Day Growth Factor |
|---|---|---|---|---|---|
| 1 | 0 | 0 | NA | $7.94 \times 10^5$ | NA |
| 2 | 0 | 0 | $5.00 \times 10^5$ | $5.95 \times 10^5$ | 1.19 |
| 3 | 1 | 1 | $5.00 \times 10^5$ | $2.65 \times 10^5$ | 0.53 |
| 4 | 1 | 1 | $2.50 \times 10^5$ | $1.08 \times 10^6$ | 4.32 |

TABLE 2-continued

Passage History to Adapt aCLDK Cells to sCLDK-SF Cells

| Passage | % Pluronic® F68 Surfactant | % Lipumin™ ADCF Serum Substitute | Cell Plant Density (cells/mL) | Cell count/mL | 7-Day Growth Factor |
|---|---|---|---|---|---|
| 5 | 1 | 1 | $5.00 \times 10^5$ | $4.15 \times 10^5$ | 0.83 |
| 6 | 1 | 1 | $3.00 \times 10^5$ | $4.45 \times 10^5$ | 1.48 |
| 7 | 1 | 1 | $4.00 \times 10^5$ | $2.35 \times 10^5$ | 0.59 |
| 8 | 1 | 1 | $2.00 \times 10^5$ | $8.34 \times 10^5$ | 4.17 |
| 9 | 1 | 1 | $5.00 \times 10^5$ | $2.09 \times 10^6$ | 4.18 |
| 10 | 1 | 1 | $5.00 \times 10^5$ | $1.67 \times 10^6$ | 3.34 |
| 11 | 1 | 1 | $5.00 \times 10^5$ | $3.35 \times 10^6$ | 6.70 |
| 12 | 1 | 1 | $5.00 \times 10^5$ | $3.25 \times 10^6$ | 6.50 |
| 13 | 1 | 1 | $5.00 \times 10^5$ | $3.90 \times 10^6$ | 7.80 |
| 14 | 1 | 1 | $5.00 \times 10^5$ | $7.10 \times 10^6$ | 14.20 |
| 15 | 1 | 1 | $5.00 \times 10^5$ | $7.28 \times 10^6$ | 14.56 |
| 16 | 1 | 1 | $5.00 \times 10^5$ | $6.84 \times 10^6$ | 13.68 |
| 17 | 1 | 1 | $5.00 \times 10^5$ | $6.68 \times 10^6$ | 13.36 |
| 18 | 0.5 | 0.5 | $5.00 \times 10^5$ | $8.10 \times 10^6$ | 16.20 |
| 19 | 0.25 | 0.25 | $5.00 \times 10^5$ | $7.37 \times 10^6$ | 14.74 |
| 20 | 0.125 | 0.125 | $5.00 \times 10^5$ | $2.76 \times 10^6$ | 5.52 |
| 21 | 0 | 0 | $5.00 \times 10^5$ | $6.87 \times 10^6$ | 13.74 |
| 22 | 0 | 0 | $5.00 \times 10^5$ | $7.42 \times 10^6$ | 14.84 |
| 23 | 0 | 0 | $5.00 \times 10^5$ | $7.80 \times 10^6$ | 15.60 |
| 24 | 0 | 0 | $5.00 \times 10^5$ | $1.00 \times 10^7$ | 20.00 |

Example 1C

Procedure for Recovering sCLDK-SF MCS Cells from Liquid Nitrogen Storage and Optimum Growth Propagation 1 L of supplemented EX-CELL™ MDCK serum-free medium was prepared using an aseptic technique. Thereafter, 2-3 mLs of cells from the frozen ampoules of passage 41 of Example 1A were retrieved from liquid nitrogen and allowed to thaw. The thawed ampoules were sprayed with 70% alcohol and allowed to dry. A sterile ampoule snapper was used to break open all vials. Thereafter, a sterile pipette was used to transfer an ampoule of cells to a small sterile tube with cap (sterile 4.5 mL cryovial or equivalent). This step was repeated for the second and third ampoules.

With a sterile pipette, 1.0 mL of supplemented EX-CELL™ MDCK serum free medium was added to each tube. After these tubes containing the cell-medium mixture sat for approximately 3-5 minutes, a sterile pipette was used to transfer cell-medium mixture from one small sterile tube to a 15 mL centrifuge tube (Falcon or equivalent). This step was repeated for the second and third small tubes containing cell-media mixture. Approximately 8.0 mLs of supplemented EX-CELL™ MDCK Serum free medium was added to each tube. After allowing all 15 mL centrifuge tubes containing 10 mLs each of cell-medium mixture to sit for 5-10 minutes, the tubes were centrifuged for 10 minutes at approximately 500×g. The media was then poured out of the centrifuge tubes while keeping the pellet(s). Approximately 5 mLs of supplemented EX-CELL™ MDCK serum free medium was added to each centrifuge tube with a sterile pipette. The pellets were then re-suspended in the centrifuge tubes. The re-suspended cell-media mixtures from all tubes were transferred into one 125 mL shaker flask fitted with a 0.2 μl vented cap. Approximately 40 mLs of supplemented EX-CELL™ MDCK serum free media was then added to the 125 mL shaker flask, which was then placed on an orbital shaker (100-110 RPM) inside a 37° C. incubator set at 10% $CO_2$. The cells were incubated four to seven days. Seven days yielded the highest cell growth factors without a substantial loss in viability. Cell and viability count were performed using an automated mammalian cell counter.

Example 1D

Procedure for Passing sCLDK-SF MCS Cells for Growth Propagation

The following procedure was optimized for continuous growth of sCLDK-SF cells. This process begins after recovering cells as in Example 1C, and can be repeated every 7 days to maintain continuous cell growth. Cells are grown in supplemented EX-CELL™ MDCK serum-free medium.

After retrieving a shaker flask containing live sCLDK-SF cells in supplemented EX-CELL™ MDCK serum free medium from the incubator, a sterile pipette is used to transfer a cell sample from the shaker flask to a sample vial. Cell and viability count is performed using an automated or manual means of counting. Once counts are performed, the total volume of cells needed to plant a new shaker flask with 50 mLs at a cell density of $5.0 \times 10^5$ cells/mL (or, $2.5 \times 10^7$ cells/125 mL shaker flask) is calculated.

The calculated volume of cells is transferred via sterile pipette to a new 125 mL shaker flask. After adding the appropriate volume of supplemented EX-CELL™ MDCK serum-free medium for a total volume of 50 mL, the shaker flask is placed on an orbital shaker (100-110 RPM). Cells are maintained undisturbed at 37° C. in the incubator with 10% $CO_2$ for a seven day period. This process can be repeated once every 4-10 days to maintain cells constantly. The following data is representative of serial passages for continuous cell growth. Passages 1-16 occurred weekly, and passages 17-34 occurred every four days.

TABLE 3

Continuous Cell Growth of sCLDK-SF Over 34 Passages

| Pass # | Cell plant density (cells/mL) | Cell count (cells/mL) | Growth Factor | Viability |
|---|---|---|---|---|
| MCS | NA | NA | NA | NA |
| 1 | NA | $4.16 \times 10^6$ | NA | 93.99% |
| 2 | $5.00 \times 10^5$ | $7.72 \times 10^6$ | 15.44 | 96.65% |
| 3 | $5.00 \times 10^5$ | $3.49 \times 10^7$ | 69.80 | 99.99% |
| 4 | $5.00 \times 10^5$ | $2.69 \times 10^6$ | 5.38 | 99.66% |
| 5 | $5.00 \times 10^5$ | $1.35 \times 10^7$ | 27.00 | 98.13% |
| 6 | $5.00 \times 10^5$ | $1.30 \times 10^7$ | 26.00 | NA |
| 7 | $5.00 \times 10^5$ | $1.04 \times 10^7$ | 20.80 | 95.24% |
| 8 | $5.00 \times 10^5$ | $3.86 \times 10^6$ | 7.72 | 98.83% |
| 9 | $5.00 \times 10^5$ | $4.82 \times 10^6$ | 9.64 | 96.76% |
| 10 | $5.00 \times 10^5$ | $1.36 \times 10^7$ | 27.20 | 98.96% |
| 11 | $5.00 \times 10^5$ | $7.29 \times 10^6$ | 14.58 | 99.60% |
| 12 | $5.00 \times 10^5$ | $1.22 \times 10^7$ | 24.40 | 99.52% |
| 13 | $5.00 \times 10^5$ | $9.56 \times 10^6$ | 19.12 | 99.52% |
| 14 | $5.00 \times 10^5$ | $1.17 \times 10^7$ | 23.40 | 99.64% |
| 15 | $5.00 \times 10^5$ | $1.08 \times 10^7$ | 21.60 | 99.58% |
| 16 | $5.00 \times 10^5$ | $1.05 \times 10^7$ | 21.00 | 99.50% |
| 17 | $5.00 \times 10^5$ | $3.56 \times 10^6$ | 7.12 | 99.75% |
| 18 | $5.00 \times 10^5$ | $1.03 \times 10^7$ | 20.60 | 99.75% |
| 19 | $5.00 \times 10^5$ | $1.19 \times 10^7$ | 23.80 | 99.26% |
| 20 | $5.00 \times 10^5$ | $6.20 \times 10^6$ | 12.40 | 99.87% |
| 21 | $5.00 \times 10^5$ | $1.10 \times 10^7$ | 22.00 | 99.39% |
| 22 | $5.00 \times 10^5$ | $2.99 \times 10^6$ | 5.98 | 99.66% |
| 23 | $5.00 \times 10^5$ | $1.26 \times 10^7$ | 25.2 | 99.14% |
| 24 | $5.00 \times 10^5$ | $1.53 \times 10^7$ | 30.60 | 99.96% |
| 25 | $5.00 \times 10^5$ | $7.60 \times 10^6$ | 15.20 | 98.00% |
| 26 | $5.00 \times 10^5$ | $1.34 \times 10^7$ | 26.80 | 99.32% |
| 27 | $5.00 \times 10^5$ | $1.12 \times 10^7$ | 22.40 | 99.00% |
| 28 | $5.00 \times 10^5$ | $8.47 \times 10^6$ | 16.94 | 99.77% |
| 29 | $5.00 \times 10^5$ | $6.92 \times 10^6$ | 13.84 | 99.85% |
| 30 | $5.00 \times 10^5$ | $9.58 \times 10^6$ | 19.16 | 99.78% |

TABLE 3-continued

Continuous Cell Growth of sCLDK-SF Over 34 Passages

| Pass # | Cell plant density (cells/mL) | Cell count (cells/mL) | Growth Factor | Viability |
|---|---|---|---|---|
| 31 | $5.00 \times 10^5$ | $7.33 \times 10^6$ | 14.66 | 99.78% |
| 32 | $5.00 \times 10^5$ | $9.26 \times 10^6$ | 18.52 | 99.83% |
| 33 | $5.00 \times 10^5$ | $6.76 \times 10^6$ | 13.52 | 99.63% |
| 34 | $5.00 \times 10^5$ | $1.13 \times 10^7$ | 22.60 | 99.81% |

Example 2

Comparative Growth of aCLDK Cells to sCLDK-SF Cells in Suspension in Different Serum-Free Media aCLDK cells were taken out of storage in liquid nitrogen and were grown in a 75 cm² flask for approximately 48 hours using 10% FBS in Eagle's Minimum Essential Medium (EMEM). The cells were then transferred to an 850 cm² roller bottle with 5% Fetal Bovine Serum and EMEM media. This roller was then trypsinized; cells were harvested and planted into two different 125 ml shaker flasks at a cell density of $5.0 \times 10^5$ cells/mL. Of these two flasks, one flask contained supplemented EX-CELL™ MDCK serum-free medium and the other flask contained EMEM medium. A third flask containing sCLDK-SF cells (from an available continuous stock) were planted at a cell density of $5.0 \times 10^5$ cells/mL in supplemented EX-CELL™ MDCK serum-free medium. The three suspension flasks were then placed on an orbital shaker in a 37° C. water jacketed incubator and sampled daily (see results below) for cell and viability counts.

TABLE 4

Growth of sCLDK in Supplemented EX-CELL™ MDCK Serum-Free Medium

| Day | Amount of Cell Plant | Viability | Growth Factor |
|---|---|---|---|
| 0 | $5.00 \times 10^5$ | not measured | 1.0 |
| 1 | $1.28 \times 10^5$ | 82.81% | 0.3 |
| 2 | $5.31 \times 10^5$ | 98.30% | 1.0 |
| 3 | $1.16 \times 10^6$ | 99.48% | 2.3 |
| 4 | $2.15 \times 10^6$ | 99.72% | 4.3 |
| 5 | $4.46 \times 10^6$ | 99.75% | 8.9 |
| 6 | $6.88 \times 10^6$ | 99.73% | 13.8 |
| 7* | $1.09 \times 10^7$ | 99.77% | 21.8 |
| 8 | $5.35 \times 10^5$ | 99.06% | 1.1 |
| 9 | $1.47 \times 10^6$ | 99.65% | 2.9 |
| 10 | $3.30 \times 10^6$ | 99.99% | 6.6 |
| 11 | $7.37 \times 10^6$ | 99.91% | 14.7 |
| 12 | $1.21 \times 10^7$ | 99.80% | 24.2 |
| 13 | $1.28 \times 10^7$ | 99.73% | 25.6 |
| 14* | $1.55 \times 10^7$ | 99.80% | 31.1 |
| 15 | $4.45 \times 10^5$ | 98.87% | 0.9 |
| 16 | $8.35 \times 10^5$ | 99.40% | 1.7 |
| 17 | $2.37 \times 10^6$ | 99.78% | 4.7 |
| 18 | $6.81 \times 10^6$ | 99.93% | 13.6 |
| 19 | $9.33 \times 10^6$ | 99.69% | 18.7 |
| 20 | $1.29 \times 10^7$ | 99.65% | 25.9 |
| 21 | $1.33 \times 10^7$ | 99.77% | 26.6 |

*Cells were passed into fresh media every seven days.

TABLE 5

Growth of aCLDK in EMEM Media (No Serum)

| Day | Amount of Cell Plant | Viability | Growth Factor |
|---|---|---|---|
| 0 | $5.00 \times 10^5$ | | 1.0 |
| 1 | $5.30 \times 10^5$ | 98.11% | 1.1 |
| 2 | $4.75 \times 10^5$ | 98.94% | 1.0 |
| 3 | $5.05 \times 10^5$ | 99.00% | 1.0 |
| 4 | $4.45 \times 10^5$ | 98.87% | 0.9 |
| 5 | $3.55 \times 10^5$ | 98.59% | 0.7 |
| 6 | $3.85 \times 10^5$ | 98.70% | 0.8 |
| 7* | $3.85 \times 10^5$ | 98.70% | 0.8 |
| 8 | $1.75 \times 10^5$ | 97.14% | 0.4 |
| 9 | $1.45 \times 10^5$ | 96.55% | 0.3 |
| 10 | $1.75 \times 10^5$ | 97.14% | 0.4 |
| 11 | $1.90 \times 10^5$ | 97.36% | 0.4 |
| 12 | $1.51 \times 10^5$ | 96.68% | 0.3 |
| 13 | $1.30 \times 10^5$ | 96.15% | 0.3 |
| 14* | $1.06 \times 10^5$ | 95.28% | 0.0 |
| 15 | ** | ** | ** |

*Cells were passed into fresh media every seven days.

** For this study to plant a shaker flask at proper density, a cell density must be at least $5 \times 10E5$, this cell count was not high enough to plant an adequate (25-50 mL) amount in a shaker flask. Therefore these cells were discarded.

TABLE 6

Growth of aCLDK in Supplemented EX-CELL™ MDCK Serum-Free Medium

| Day | Amount of Cell Plant | Viability | Growth Factor |
|---|---|---|---|
| 0 | $5.00 \times 10^5$ | | 1.0 |
| 1 | $8.65 \times 10^5$ | 99.42% | 1.7 |
| 2 | $9.25 \times 10^5$ | 99.45% | 1.9 |
| 3 | $1.20 \times 10^6$ | 99.58% | 2.4 |
| 4 | $1.28 \times 10^6$ | 99.45% | 2.6 |
| 5 | $1.47 \times 10^6$ | 99.65% | 2.9 |
| 6 | $1.65 \times 10^6$ | 99.69% | 3.3 |
| 7* | $1.23 \times 10^6$ | 99.59% | 2.5 |
| 8 | $4.45 \times 10^5$ | 98.87% | 0.9 |
| 9 | $5.35 \times 10^5$ | 99.06% | 1.1 |
| 10 | $8.95 \times 10^5$ | 99.44% | 1.8 |
| 11 | $8.05 \times 10^5$ | 99.37% | 1.6 |
| 12 | $7.45 \times 10^5$ | 99.32% | 1.5 |
| 13 | $8.95 \times 10^5$ | 99.44% | 1.8 |
| 14* | $9.25 \times 10^5$ | 99.45% | 1.9 |
| 15 | $5.65 \times 10^5$ | 99.11% | 1.1 |
| 16 | $6.55 \times 10^5$ | 99.23% | 1.3 |
| 17 | $8.65 \times 10^5$ | 99.42% | 1.7 |
| 18 | $7.45 \times 10^5$ | 99.32% | 1.5 |
| 19 | $8.05 \times 10^5$ | 99.37% | 1.6 |
| 20 | $7.75 \times 10^5$ | 99.35% | 1.6 |
| 21 | $6.55 \times 10^5$ | 99.23% | 1.3 |

*Cells were passed into fresh media every seven days.

From this study it can be concluded that the aCLDK cells in EMEM medium do not grow in suspension culture. The data also shows that aCLDK in supplemented EX-CELL™ MDCK serum-free medium do not grow at a sufficient rate to be considered a viable alternative for production. Typically a growth factor of at least 5 is required to be considered useful for production. Instead, these cells simply maintained their cell density and viability. Lastly this study shows that the sCLDK-SF cells in supplemented EX-CELL™ MDCK serum-free medium grow very well serum free in suspension with an average split ratio above 10 and maintain a high (>99%) viability.

Example 3

Attempted Adaptation of Substrate-Dependent CLDK Cells for Suspended Growth in Different Media Containing Serum Two cryovials of aCLDK cells were removed from liquid nitrogen tank and thawed. The material in one vial was resuspended in 10 mL of supplemented EX-CELL™ MDCK serum-free medium, further supplemented with 5% fetal bovine serum (FBS). The material in the other vial was resuspended in 10 mL of supplemented Hank's minimal essential medium (MEMH). Supplemented MEMH medium is described in U.S. Pat. No. RE 33,164 (from U.S. Pat. No. 4,500,513), which is hereby wholly incorporated by reference. This medium as used in this example includes the following:

Fetal Bovine Serum (FBS), 5%
Non-Essential Amino Acids, 10 ml/L media
L-Glutamine, 10 mL/L media
Neomycin Sulfate, (0.3 mL of 100 mg/mL stock solution)/L media
Polymyxin B, 30,000 units/L media
Nystatin, 25,000 units/L media
50% Dextrose, 2.6 ml/L media
MEM Vitamins, 30 mL/L media Both vials were centrifuged and the supernatant was discarded. Cell pellets were then separately resuspended in 10 mLs of their respective medium and then transferred to separate 25 mL tissue culture flasks with 25 mL total volume of their respective medium (both media contained 5% FBS). Both flasks were placed into a 35° C. incubator.

The following day, both tissue flasks were observed under microscope and found to be 90-100% confluent. Both flasks were trypsinized and cells were transferred to appropriate 490 cm$^2$ roller bottles and placed in a total volume of 150 mL of media/roller bottle. Both rollers were placed onto a roller cart (0.3 rpm) in a 35° C. incubator. Three days later, cells in both roller bottles were observed microscopically and found to be 30% confluent. Another three days later, cell and viability counts were performed. The cells in the MEMH were found to contain $1.02 \times 10^7$ cells/mL that were 99.5% viable. The cells in the supplemented EX-CELL™ MDCK serum-free medium with 5% FBS were found to contain $1.09 \times 10^7$ cells/mL that were 99.83% viable. Both roller bottles were trypsinized and cells were passed into new 490 cm$^2$ roller bottles at a cell density of $3.16 \times 10^5$ cells/mL and placed in a total volume of 150 mL of media/roller bottle. Both rollers were placed into a 35° C. incubator.

Four days after being in the incubator, cell and viability counts were performed. The material in the Hanks MEM was found to contain $1.12 \times 10^7$ cells/mL, with 99.5% of the cells being viable. The material in the supplemented EX-CELL™ MDCK serum-free medium with 5% FBS was found to contain $1.27 \times 10^7$ cells/mL with 89.69% of the cells being viable. Both roller bottles were trypsinized and the cells were passed into new 490 cm$^2$ roller bottles at a cell density of $3.16 \times 10^5$ cells/mL and placed in a total volume of 150 mL of media/roller bottle. Both rollers were placed into a 35° C. incubator.

Five days after being in the incubator, cell and viability counts were again performed. The material in the Hank's MEM was found to contain $1.03 \times 10^7$ cells/mL with 99.9% of the cells being viable. The material in the supplemented EX-CELL™ MDCK serum-free medium with 5% FBS was found to contain $1.72 \times 10^7$ cells/mL with 91.91% of the cells being viable. Both roller bottles were trypsinized and cells were passed into new 490 cm$^2$ roller bottles at a cell density of $3.16 \times 10^5$ cells/mL and placed in a total volume of 150 mL of media/roller bottle. Both rollers were placed back into a 35° C. incubator.

Four days after being in the incubator, cell and viability counts were again performed. The material in the Hanks MEM was found to contain $5.95 \times 10^6$ cells/mL with 99.2% of the cells being viable. The material in the supplemented EX-CELL™ MDCK serum-free medium with 5% FBS was found to contain $9.41 \times 10^6$ cells/mL with 85.84% of the cells being viable. Both roller bottles were trypsinized and the cells were passed into new 125 mL shaker flasks at a cell density of $3.16 \times 10^5$ cells/mL and placed in a total volume of 50 mL of media/shaker flask. Both shaker flasks were placed onto an orbital shaker at 100-110 rpm in a 35° C. incubator.

Four days after being in the incubator, cell and viability counts were again performed. The material in the Hanks MEM was found to contain $2.15 \times 10^5$ cells/mL with 94.0% of the cells being viable. The material in the supplemented EX-CELL™ MDCK serum-free medium with 5% FBS was found to contain $1.38 \times 10^6$ cells/mL with 99.6% of the cells being viable. Both shaker flasks were placed back onto the orbital shaker at 100-110 rpm in a 35° C. incubator.

Three days after being in the incubator, cell and viability counts were again performed. The material in the Hanks MEM was found to contain $2.00 \times 10^5$ cells/mL (corresponding to a growth factor of 0.63) with 95.0% of the cells being viable. The material in the supplemented EX-CELL™ MDCK serum-free medium with 5% FBS was found to contain $3.03 \times 10^6$ cells/mL (corresponding to a growth factor of 9.58) with 99.8% viable of the cells being viable. The CLDK cells in the supplemented EX-CELL™ MDCK serum-free medium with 5% FBS medium were then planted in a new 125 mL shaker flask at a cell density of $3.16 \times 10^5$ cells/mL and placed on an orbital shaker in 35° C. incubator to determine whether the cells would continue to grow and placed in a total volume of 50 mL of media/shaker flask.

Seven days after being in the incubator, cell and viability counts were again performed. The CLDK cells in the supplemented EX-CELL™ MDCK serum-free medium with 5% FBS media were found to contain less than $1.5 \times 10^5$ cells/mL. The viability count could not be performed with the nucleocounter because values were too low. Visually, cells were very clumpy, and the cell culture was discarded.

The above passage protocol is summarized in the table below. Passages 2 through 5 were done in roller bottles, which is customary for culturing substrate-dependent cells. Below the double line, passages 6 and 7 were done in shaker flasks to attempt adaptation of the cells for suspended growth. As is evident from the table, however, the cell density dropped rapidly despite lengthier incubation periods after only 1 passage in shaker flasks. Indeed, the cells did not grow sufficiently to continue the experiment after only one transfer into shaker flasks for the material in the Hank's MEM medium, and after only two transfers into shaker flasks for the material in the supplemented EX-CELL™ MDCK serum-free medium. This data indicates that these substrate-dependent CLDK cells do not grow in suspension.

TABLE 7

Summary of Attempted Adaptation of Substrate-Dependent CLDK Cells for Suspended Growth in Different Media Containing Serum

| Passage Number | Concentration of material being planted into fresh media. | Incubation period of culture material being measured | Hank's MEM cells/mL | viability | EX-CELL MDCK cells/mL | viability |
|---|---|---|---|---|---|---|
| 2* | everything transferred from initial breakout from cryovials | 6 | $1.02 \times 10^7$ cells/mL | 99.5 | $1.09 \times 10^7$ cells/mL | 99.83 |
| 3 | $3.16 \times 10^5$ cells/mL | 4 | $1.12 \times 10^7$ cells/mL | 99.5% | $1.27 \times 10^7$ cells/mL | 89.69% |
| 4 | $3.16 \times 10^5$ cells/mL | 5 | $1.03 \times 10^7$ cells/mL | 99.9 | $1.72 \times 10^7$ cells/mL | 91.91 |
| 5 | $3.16 \times 10^5$ cells/mL | 4 | $5.95 \times 10^6$ cells/mL | 99.2 | $9.41 \times 10^6$ cells/mL | 85.84 |
| 6 | $3.16 \times 10^5$ cells/mL | 4 | $2.15 \times 10^5$ cells/mL | 94.0 | $1.38 \times 10^6$ cells/mL | 99.6 |
| No passage; same shaker flasks returned to incubation. | | 3 | $2.00 \times 10^5$ cells/mL | 95.0 | $3.03 \times 10^6$ cells/mL | 99.8 |
| 7 | $3.16 \times 10^5$ cells/mL | 7 | Not enough material to continue with culturing. | | $<1.5 \times 10^5$ cells/mL | not measurable; cells clumpy |

*The first passage involved steps immediately after breaking the cells out of liquid nitrogen.

Example 4

Infection of sCLDK Cells with Influenza Virus

The sCLDK-SF cell line was infected with Canine flu (CIV, A/canine/Miami/05), a cold-adapted temperature sensitive H3N8 influenza (A/equine/2/Kentucky/1/91, described in U.S. Pat. No. 6,177,082, which is hereby wholly incorporated by reference), and a third H3N8 influenza virus (KY02, equine/Kentucky/02). When screened for HA, all three harvested viruses tested returned positive HA results, with CIV and KY02 showing a significant amount of titer. Titer data was not collected for the cold-adapted temperature sensitive H3N8 influenza virus tested.

sCLDK-SF cells were grown in supplemented EX-CELL™ MDCK serum-free medium prior to planting, most typically for 5-7 days. Cells were harvested from shaker flasks and planted at desired densities ($1.0 \times 10^6$ cells/mL), in supplemented EX-CELL™ MDCK serum-free medium media at 50.0 mL per shaker flask (one flask per each virus) and incubated at 37° C. on a shaker orbital with 10% $CO_2$. One hour post plant, shakers were infected with appropriate virus and multiplicity of infection (MOI), see table below. Trypsin is added, 1 mL per liter (50 microliters per 50 mL). CIV and KYO2 are incubated at 37° C., Flu-Avert at 34° C. Infected shaker flask(s) were observed daily and percent of infection was monitored and recorded. Daily samples were taken and frozen at −70° C. to screen later for HA titer. Once it was determined that 90-100% of cells were infected, cells were harvested and frozen at −70° C. Frozen samples were taken daily and tested for HA.

TABLE 8

Results: HA Testing

| Flask | Virus | MOI | Est. titer | Temp. | HA* | Actual Titer (log base 2) |
|---|---|---|---|---|---|---|
| 1 | CIV | 0.01 | 6.6 log/ml | 37° C. | 1:512 | 6.3, 7.2 |
| 2 | KY02 | 0.01 | 6.0 log/ml | 37° C. | 1:128 | 6.3, 6.1, 6.5 |
| 3 | Flu-Avert | 0.01 | 4.83 log/ml | 34° C. | 1:1024-2048 | not available |
| Control | K9 Flu-Ref CIN0692001 (HA control) | NA | NA | NA | 1:64-128 | not available |

*HA refers to the hemagglutination assay. The values reflect the greatest 2-fold dilution of the material at which hemagglutination of red blood cells can be observed.
**Actual titer values are reported in log base-2.

The above detailed description is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

All publications discussed herein are wholly incorporated by reference herein.

The invention claimed is:

1. A method of replicating virus in a culture of sCLDK cells comprising:

a) inoculating a suspension of sCLDK cells with a virus, thereby infecting the sCLDK cells;

b) allowing said virus to reproduce in said infected sCLDK cells; and c) harvesting said virus from said suspension culture of sCLDK cells.

2. The method of claim 1, wherein said virus is an influenza virus.

3. The method of claim 2, wherein said influenza virus is selected from the group consisting of a human influenza virus, an avian influenza virus, an equine influenza virus, a swine influenza virus, a canine influenza virus, and a feline influenza virus.

4. The method of claim 3, wherein said influenza virus is an H3 influenza virus, an H5 influenza virus or an H7 influenza virus.

5. The method of claim 3, wherein said influenza virus is selected from the group consisting of an H5N1 influenza virus, an H3N8 influenza virus, and an H3N1 influenza virus.

6. The method of claim 1, wherein shortly before inoculating, simultaneously with inoculating, or shortly after inoculating, a protease to cleave the precursor protein of hemagglutinin is added to the suspension of sCLDK cells.

7. The method of claim 6, wherein said protease is trypsin.

8. The method of claim 1, wherein said culture of sCLDK cells was grown in serum-free medium.

9. The method of claim 1, wherein said culture of sCLDK cells was grown in medium free of any animal component derived material.

10. A process of adapting substrate-dependent CLDK cells for growth in suspension comprising
  a) inoculating a sample of substrate-dependent CLDK cells in a medium comprising one or more serum substitutes;
  b) growing said cells in suspension in said medium;
  c) serially passaging said CLDK cells in suspension in fresh batches of said medium; and
  d) weaning said CLDK cells in suspension off of said one or more serum substitutes by reducing the amount of said serum substitutes in said medium to zero.

11. The process of claim 10, wherein said medium is serum-free.

12. The process of claim 10, wherein said medium is free of animal derived components.

13. A method of continuously propagating sCLDK cells in suspension comprising:
  a) inoculating sCLDK cells into a medium;
  b) growing said sCLDK cells in suspension for a period of from about 4 to 10 days;
  c) transferring a sample of cultured material from (b) into fresh cell-free medium;
  d) and repeating (b) and (c) for a period of continuous growth.

14. The method of claim 13, wherein said medium is serum-free.

15. The method of claim 13, wherein said medium is free of animal derived components.

16. The method of claim 13, wherein said sample is transferred to said fresh cell-free medium without the prior addition of any protease.

17. The method of claim 13, wherein the cell density after transferring the sample according to (c) is at least $3 \times 10^5$ cells/mL.

18. The method of claim 13, wherein said sCLDK cells have a growth factor greater than about 3 over 4-10 days.

19. A sCLDK cell capable of growing in suspension obtainable by the process of adapting substrate-dependent CLDK cells for growth in suspension of claim 10.

20. A composition comprising cell culture medium and the sCLDK cell of claim 19.

* * * * *